United States Patent
Senn et al.

(10) Patent No.: US 10,376,350 B2
(45) Date of Patent: Aug. 13, 2019

(54) DENTAL LIGHT CURING DEVICE

(71) Applicant: Ivoclar Vivadent AG, Schaan (LI)

(72) Inventors: Bruno Senn, Buchs (CH); Dario Tommasini, Mastrils (CH)

(73) Assignee: Ivoclar Vivadent AG, Schaan (LI)

(*) Notice: Subject to any disclaimer, the term of this patent is extended or adjusted under 35 U.S.C. 154(b) by 58 days.

(21) Appl. No.: 15/735,469

(22) PCT Filed: Jun. 17, 2016

(86) PCT No.: PCT/EP2016/064029
§ 371 (c)(1),
(2) Date: Dec. 11, 2017

(87) PCT Pub. No.: WO2016/202992
PCT Pub. Date: Dec. 22, 2016

(65) Prior Publication Data
US 2018/0153668 A1  Jun. 7, 2018

(30) Foreign Application Priority Data
Jun. 17, 2015  (EP) .................................. 15172598

(51) Int. Cl.
*A61C 19/00* (2006.01)
*A61C 13/15* (2006.01)
(Continued)

(52) U.S. Cl.
CPC .......... *A61C 19/003* (2013.01); *A61C 1/0015* (2013.01); *A61C 19/004* (2013.01);
(Continued)

(58) Field of Classification Search
CPC ............................ A61C 19/003; A61C 19/004
See application file for complete search history.

(56) References Cited

U.S. PATENT DOCUMENTS

| | | | | |
|---|---|---|---|---|
| 6,835,064 B2* | 12/2004 | Burtscher | ............ | A61C 19/004 433/229 |
| 2003/0215767 A1* | 11/2003 | Taub | .................... | A61B 1/0607 433/29 |

(Continued)

*Primary Examiner* — Ralph A Lewis
(74) *Attorney, Agent, or Firm* — Ann M. Knab; Thad McMurray

(57) ABSTRACT

The invention relates to a dental light-curing device (10) provided for dental material to be cured, which comprises a handpiece (20) and a base station, wherein the handpiece (20) has a light source, in particular having a plurality of LED chips (42, 44, 46 and 48), which—with respect to the optical axis—are arranged one next to the other, a control device (22) for the light source and at least one sensor, which is arranged adjacent to the light source, wherein—again with respect to the optical axis—a light guiding device, in particular a light guide rod (12), extends in front of the light source, which light guide rod (12) has a passband for wavelengths which comprises at least blue visible light and, in particular, also green visible light and UV light, and having a selecting device for control programs of the control device (22), in particular a push button on the handpiece (20). The invention is characterized by comprising a control device (22) and also a "pre-curing" control program, which can be selected by means of the selecting device, and in which the light-curing device can be activated with a secondary wavelength range, which is different from a light-curing main wavelength range, and the light radiation of which is outside the sensitivity range of the dental material to be cured. The control device (22) automatically switches on the light source in the main wavelength range in order to pre-cure excess glue (28) in dental restorations, in particular adhesive crowns or adhesive bridges, if at least one sensor detects light reflected from a tooth surface in the secondary wavelength range.

18 Claims, 1 Drawing Sheet

(51) Int. Cl.
*B64C 1/20* (2006.01)
*B64C 1/22* (2006.01)
*B64D 9/00* (2006.01)
*A61C 1/00* (2006.01)

(52) U.S. Cl.
CPC .......... *B64C 1/20* (2013.01); *B64C 1/22* (2013.01); *B64D 9/00* (2013.01); *B64D 2009/006* (2013.01)

(56) References Cited

U.S. PATENT DOCUMENTS

| | | | |
|---|---|---|---|
| 2010/0273123 A1* | 10/2010 | Mecher | A61C 19/004 433/29 |
| 2015/0016140 A1* | 1/2015 | Weingaertner | A61B 1/0684 362/553 |
| 2015/0202032 A1* | 7/2015 | Benz | A61C 1/0015 433/27 |
| 2016/0113746 A1* | 4/2016 | Bringley | A61K 6/0017 433/29 |
| 2018/0296310 A1* | 10/2018 | Benz | A61C 19/004 |

* cited by examiner

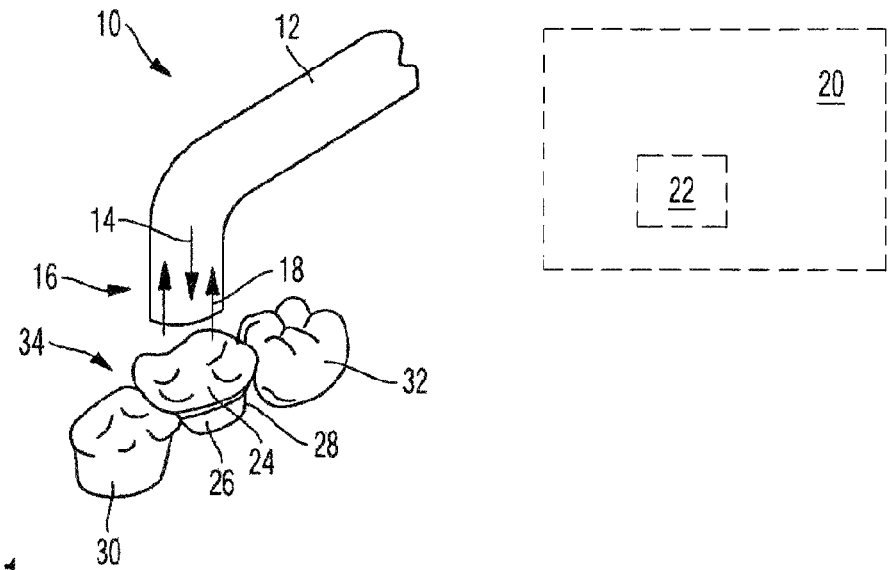
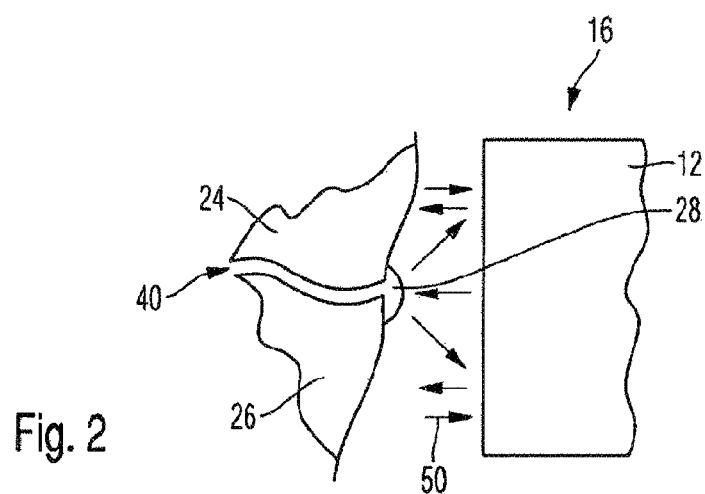
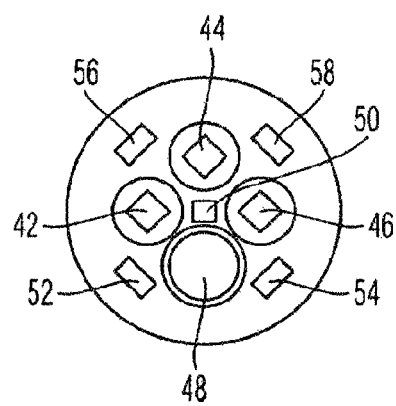

DENTAL LIGHT CURING DEVICE

CROSS-REFERENCE TO RELATED APPLICATIONS

This application is a National Stage application of International patent application PCT/EP2016/064029 filed on Jun. 17, 2016, which claims priority to European patent application No. 15172598.3 filed on Jun. 17, 2015, the disclosures of which are incorporated herein by reference in their entirety.

FIELD OF THE INVENTION

The invention relates to a dental light-curing device provided for dental material to be cured, and to a system of such a dental light-curing device and an adhesive crown or an adhesive bridge.

BACKGROUND OF THE INVENTION

Dental crowns are often glued onto tooth stumps by providing either the tooth stump or the crown or both with an adhesive suitable for this purpose and then pressing them onto one another. In order to ensure durability of the adhesive joint it is crucial that the entire areas of the adhesive surfaces are provided with the adhesive. For this purpose, it has been known for long to provide for excess adhesive and to then press the parts to be adhered to one another against each other such that excess adhesive is partially squeezed out to the side and such that it is ensured that the entire surfaces are covered with adhesive in any case.

This measure which has been known for decades is used both with dental cement and with other suitable adhesives.

Care must always be taken that the adhesion both on the surface of the respective tooth and on the opposite surface of the dental restoration has the required quality. Typically, at least the surface of the tooth is etched slightly and agents referred to as adhesion agents are used.

Depending on the material of the dental restoration used different adhesives are used. Particularly with composites, there is a tendency towards light-curable adhesives. They typically ooze out of the adhesive gap all around when the dental restoration is pressed on by means of the predetermined force.

As a matter of fact, this so-called excess adhesive must be removed wherein it is difficult particularly with light-curable adhesives to remove excess adhesive as it tends to smear.

In this respect, it has already been suggested to partially cure the excess adhesive in order to turn it gel-like and be able to simply pull it off. Tests have shown that when conventional light-curing devices are used for this purpose it is, however, difficult to remove the excess adhesive; when the material has cured too strongly, it may be ground only very expensively, or virtually not at all in the interdental spaces, and when the material has cured not sufficiently, it only smears when somebody tries to remove the material.

However, leaving excess adhesive in the mesial/distal direction, that is to say in the interdental spaces, particularly leads to periodontitis very easily as deposits and bacteria may easily collect in narrow inner corners which are difficult to access.

SUMMARY OF THE INVENTION

Thus, the invention is based on the task of providing a light-curing device provided for dental material to be cured, having a handpiece and a base station, wherein the handpiece has a light source, a control device for the light source and at least one sensor, which is arranged adjacent to the light source, wherein a light guiding device extends in front of the light source, and having a selecting device for control programs of the control device, and a matching system having a dental light curing device and an adhesive crown or an adhesive bridge, which does not have the known problems, without the need for an additional dental light-curing device.

This task is inventively solved by the attached independent claims. Advantageous developments may be taken from the subclaims.

According to the invention, it is particularly favorable that the inventive control program "pre-curing" can be activated automatically. This is ensured inventively in a particular manner by a special proximity sensor which is realized practically in an integrated fashion. As soon as the control program is selected, the light curing device or its control device, respectively, detects the approximation towards the dental restoration having excess adhesive and activates the pre-curing program automatically, when the distance is small enough to ensure reliable pre-curing in the desired manner.

The fixed timing of, for instance, two seconds ensures that the adhesive bead is cured neither too long nor too short such that it is always present in the desired gel-like state and may be removed reliably from the interdental spaces. No smearing occurs, and the need for grinding is omitted completely.

According to the invention, it is also prevented that the control program "pre-curing" is activated prematurely. In this way, it can be detected inventively when the light-emitting surface of the light guide rod of the light-curing device is sufficiently close to the surface of the tooth. For this purpose, the differences in the reflective properties between, for instance, the oral mucosa and the dental restoration or the tooth, respectively, are used. Initially, the light-curing device emits light in a secondary wavelength range, for instance, green light. This light is in a wavelength range which differs substantially from the wavelength range of the sensitivity maximum of the adhesive to be polymerized.

In the handpiece of the light-curing device a sensor is provided adjacent to the light source which detects light led back through the light guide rod. If the light-emitting surface of the light guide rod approaches the excess adhesive, the light in the secondary wavelength range is reflected with a certain intensity. The reflected light is detected by the sensor and a corresponding control signal of the control device is provided for activating the control program "pre-curing".

It is to be understood that the polymerization light is then emitted in the main wavelength range and that the light source is activated for the predetermined pre-curing time, for instance, 1 to 3 seconds.

In order to be able to differentiate more easily between the reflection light and the ambient light it is preferred to output the light in the secondary wavelength range in a pulsed manner or in sinusoidal shape. Detection in the sensor will then take place through the size of the detected amplitude of the reflected light such that ambient light is taken out of consideration automatically.

According to the invention, it is favorable if the control program "pre-curing" is activated on all four sides of, for instance, the crown, that is to say initially from the distal/vestibular side, then from the distal/lingual side, then from the mesio/lingual side and subsequently from the mesio/vestibular side.

An exact dosage allows pulling off of the excess adhesive in one bead, which makes work much easier compared to the problematic technique used up to now.

BRIEF DESCRIPTION OF THE DRAWINGS

Further advantages, details and features may be taken from the following description of an exemplary embodiment of the invention in conjunction with the drawings, in which:

FIG. 1 shows a schematic view of an inventive system made up of a light-curing device and a dental restoration with excess adhesive;

FIG. 2 shows an enlarged view of a detail of FIG. 1, namely of the excess adhesive and the front end of the light guide rod of the light-curing device; and FIG. 3 shows a schematic view of the distribution of LED light sources and sensors at the rear end of the light guide rod.

DETAILED DESCRIPTION

In the embodiment according to FIG. 1 a dental light-curing device 10 is provided of which only a light guide rod 12 is apparent in FIG. 1 as part of a handpiece. Additionally, the light-curing device comprises a base station, at least one storage location, in a way known per se.

At the end of the light guide rod 12 close to the housing a light source is provided which comprises preferably several LED chips. The LED chips provide the light to the light guide rod 12 and it is emitted from a front end 16 of the light guide rod 12 in accordance with the arrow 14.

Any light reflected in accordance with the arrows 18 is guided through the light guide rod 12 and enters sensors which are arranged in the area of the LED chips. It is referred to FIG. 3 for the detailed configuration.

Even if the invention is here described with reference to a light guide rod, it is to be understood that instead any other light guide devices, for instance, flexible light guides, may be realized without leaving the scope of the invention.

In the handpiece 20 which is illustrated schematically a control device 22 is provided which can execute different control programs. The selection of the control programs takes place automatically in some cases, but also, in other cases, by means of a selecting device which may be realized as a push button on the handpiece, for instance.

One of the control programs is referred to as "pre-curing" herein and is used inventively as is described in a more detailed manner herein.

The light-curing device 10 illustrated in FIG. 1 provides light to a dental restoration 24 which is adhered to a tooth stump 26. The dental restoration is pressed onto it after the adhesive has been applied in a soft state such that excess adhesive 28 is squeezed out of the adhesive gap circumferentially to the sides.

This is apparent from FIG. 2 in an enlarged illustration.

Adjacent to the dental restoration 24 in the mesial or distal direction, respectively, neighboring teeth 30 and 32 are arranged such that the interdental space 34 is rather restricted in a way known per se.

According to FIG. 2, there is an adhesive gap 40, whose width is illustrated exaggeratedly in FIG. 2, between the dental restoration 24 and the tooth stump 26. The excess adhesive 28 is provided in the manner of a bead to the sides of the adhesive gap. According to the invention, it is irradiated with radiation by means of the end 16 of the light guide rod 12 of the light-curing device 10.

It is also referred to FIG. 3 for an illustration of the process.

FIG. 3 shows three LED chips having a first wavelength emission maximum of, for instance, 470 nm. A further LED chip 48 emits light having an emission maximum of 410 nm. This range, and the range surrounding this range, presents the main wavelength range. Additionally, an LED chip 50 is provided for a secondary wavelength range in FIG. 3 which is arranged centrally in the embodiment of FIG. 3. For instance, green light may be detected therein.

Sensors 52, 54, 56 and 58 surrounding the LED chips 42, 44, 46 are provided which detect the reflected radiation.

In operation, the LED chip in the secondary wavelength range 50 is initially activated. The control device 22 detects when the end 16 according to FIG. 2 approaches the dental restoration 24 and thus the excess adhesive 28. According to the arrows 60, the emitted radiation is reflected thereat and guided to the sensors 52 to 58 by means of the light guide rod 12. When this is the case, the light source in a main wavelength range is inventively activated, that is to say via the chips 42, 44, 46 and 48, for instance for 2.2 seconds, such that excess adhesive 28 is turned gel-like.

This procedure is carried out from four spatial corners—with reference to the dental restoration 24—in order to ensure a uniform gelation process of the excess adhesive 28.

Subsequent thereto, the light-curing device 10 is turned off automatically and the gel-like excess adhesive 28 may be removed easily by hand.

It is to be understood that the type of radiation and also the duration of the exposure may be adapted to the requirements to a large extent in the "pre-curing program". Also, during activation of the light-curing device in the main wavelength range, the sensors may remain active such that it is possible to control the exposure carried out.

In a further embodiment it is provided to relocate the light source in the handpiece to the front end of a rod which is then not configured as a light guide rod but as a voltage supply and cooling rod. The associated sensor 30 is then also disposed at the front end of the handpiece, in fact next to the light source, preferably radially outside thereof.

The invention claimed is:

1. A dental light-curing device (10) provided for dental material to be cured, which comprises
a handpiece (20) and
a base station,
wherein the handpiece (20) has a light source,
a control device (22) for the light source and
at least one sensor, which is arranged adjacent to the light source, with respect to an optical axis
a light guiding device extends in front of the light source, which light guiding device has a passband for wavelengths which comprises at least blue visible light and
a selecting device for control programs of the control device (22), characterized
in that the control device (22) also comprises a "pre-curing" control program, which can be selected by means of the selecting device, and
in which the light-curing device can be activated with a secondary wavelength range, which is different from a light-curing main wavelength range, and the light radiation of which is outside the sensitivity range of the dental material to be cured, and
in that the control device (22) is configured to automatically switches on the light source in the main wavelength range in order to pre-cure excess glue (28) in dental restorations if at least one sensor detects light reflected from a tooth surface in the secondary wavelength range.

2. The dental light-curing device as claimed in claim 1, characterized in that the activation time of the light source in the main wavelength range for pre-curing for the removal of excess glue of the crown applied with glue is less than 3 seconds and ends automatically.

3. The dental light-curing device as claimed in claim 1, characterized in that the secondary wavelength range is in the range of green light.

4. The dental light-curing device as claimed in claim 1, characterized in that the sensor has a spectral sensitivity range which covers the range between 400 nm and 570 nm and a sensitivity maximum between 460 nm and 480 nm.

5. The dental light-curing device as claimed in claim 1, characterized in that the light guiding device comprises a light guide rod (12) which is exchangeable and comprises an offset end, and in that the light guide rod (12) may be exchanged with a light guide rod (12) having an offset angle which is considerably more than 45°.

6. The dental light-curing device as claimed in claim 1, characterized in that the light source comprises
several LED chips (42, 44, 46 and 48) which are arranged symmetrically relative to one another on one plane and are mounted on a common printed board, and
one LED chip (50) emitting in the secondary wavelength range,
wherein the several LED chips (42, 44, 46 and 48) are emitting in the main wavelength range.

7. The dental light-curing device as claimed in claim 1, characterized in that the light source comprises a plurality of LED chips (42, 44, 46 and 48) and at least one sensor is arranged immediately adjacent to a reflector of an LED chip (42, 44, 46 and 48) of the light source.

8. A dental light-curing device (10) provided for dental material to be cured, which comprises
a handpiece (20) and
a base station,
wherein the handpiece (20) has a light source,
a control device (22) for the light source,
at least one sensor, which is arranged adjacent to the light source,
wherein the light source emits light in a blue and/or light blue light range, and
having a selecting device for control programs of the control device (22), characterized
in that the control device (22) also comprises a "pre-curing" control program, which can be selected by means of the selecting device, and
in which the light-curing device can be switched on with a secondary wavelength range, which is different from a light-curing main wavelength range, and the light radiation of which is outside the sensitivity range of the dental material to be cured, and
in that the control device (22) is configured to automatically switches on the light source in the main wavelength range in order to pre-cure excess glue (28) in dental restorations if at least one sensor detects the light reflected from a tooth surface in the secondary wavelength range.

9. The dental light-curing device as claimed in claim 3, wherein the range of green light comprises a narrow-band range having a wavelength spectrum of about 10 nm in the green light spectrum.

10. The dental light-curing device as claimed in claim 5 wherein the light guide rod (12) used for pre-curing excess glue in the distal region of molars may have an offset angle between 60° and 80°.

11. The dental light-curing device (10) as claimed in claim 8,
wherein the light source comprises a plurality of LED chips (42, 44, 46 and 48), which, with respect to the optical axis, are arranged one next to another,
wherein the light source emits light also in a green light range and in a UV light range,
wherein the selecting device comprises a push button on the handpiece (20), and
wherein the dental restorations comprise adhesive crowns or adhesive bridges.

12. The dental light-curing device as claimed in claim 6, wherein the several LED chips comprise two to ten LED chips.

13. The dental light-curing device as claimed in claim 1, characterized in that the control device (22) switches on the light source in the main wavelength range when the amplitudes of the reflected light measured by the sensor exceed a threshold value which is predetermined by the ratio between impulse and pause of the activation of the light source with the secondary wavelength range.

14. A system comprising a dental light-curing device (10) as claimed in claim 1 and an adhesive crown or an adhesive bridge.

15. The dental light-curing device as claimed in claim 1,
wherein the light source comprises a plurality of LED chips (42, 44, 46 and 48), which, with respect to the optical axis, are arranged one next to another,
wherein the light guiding device comprises a light guide rod (12),
wherein the passband for wavelengths comprises also green visible light and UV light,
wherein the selecting device comprises a push button on the handpiece (20), and
wherein the dental restorations comprise adhesive crowns or adhesive bridges.

16. The dental light-curing device as claimed in claim 1, characterized in that the light source comprises a plurality of LED chips (42, 44, 46 and 48) and at least one sensor is arranged adjacent to two reflectors of two adjacent LED chips (42, 44, 46 and 48).

17. The dental light-curing device as claimed in claim 2, wherein the activation time is 1 to 2 seconds and ends automatically.

18. The dental light-curing device as claimed in claim 1, characterized in that the light source emits pulsed light in the secondary wavelength range for detection of the tooth surface.

* * * * *